United States Patent [19]

Sakuta et al.

[11] Patent Number: 4,960,898
[45] Date of Patent: Oct. 2, 1990

[54] ORGANOSILICON COMPOUNDS

[75] Inventors: Koji Sakuta; Satoshi Kuwata; Shigeru Mori, all of Gunma, Japan

[73] Assignee: Shin-Etsu Chemical Co., Ltd., Tokyo, Japan

[21] Appl. No.: 494,026

[22] Filed: Mar. 15, 1990

[30] Foreign Application Priority Data

Mar. 16, 1989 [JP] Japan .................................. 1-64485

[51] Int. Cl.$^5$ .............................................. C07F 7/10
[52] U.S. Cl. .................................................... 548/110
[58] Field of Search ......................................... 548/110

[56] References Cited

U.S. PATENT DOCUMENTS 4,803,254  2/1989  Dunks et al. ......................... 525/477

FOREIGN PATENT DOCUMENTS 1457966  9/1966  France .

Primary Examiner—Richard L. Raymond
Attorney, Agent, or Firm—Millen, White & Zelano

[57] ABSTRACT

Organosilicon compounds represented by the general formula:

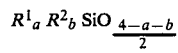

and preparing process thereof were disclosed; where a lies in the range $1 \leq a \leq 3$ and b lies in the range $0.001 \leq b \leq 2$,

$R^1$ are identical or dissimilar monovalent saturated or unsaturated hydrocarbons with 1-30 carbon atoms, $R^2$ is a monovalent organic group represented by

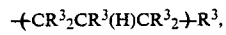

$R^3$ are hydrogen atoms or monovalent saturated hydrocarbon groups with 1-5 carbon atoms.

$R^4$ are monovalent organic groups represented by the formula:

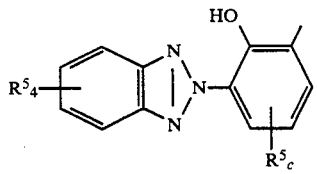

or:

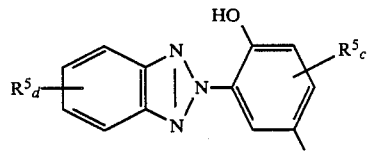

$R^5$ being identical to said $R^1$ or halogen atoms, alkoxy groups, carboxyl groups, hydroxyl groups or amino groups, d is an integer from 0 to 4 and c is an integer from 0 to 3.

9 Claims, 10 Drawing Sheets

ORGANOSILICON COMPOUNDS

FIELD OF THE INVENTION

This invention concerns organosilicon compounds soluble in silicone oils, and more particularly, novel organosilicon compounds which strongly absorb ultraviolet radiation.

BACKGROUND OF THE INVENTION

Ultraviolet absorbing compounds with a benzotriazole skeleton have conventionally been used as blending agents in medical preparations and cosmetics, or as additives to plastics. These compounds however all have poor dispersibility and solubility in substrates, and as there was a limit to their blending proportion and stability in dispersion, they suffered from bleeding and other disadvantages.

Further, although silicone oils find application in a variety of different fields, benzotriazole type compounds suffered from the disadvantage of being difficulty soluble in silicone oils.

To remedy these disadvantages, alkoxysilyl groups may for example be introduced into the benzotriazole skeleton, and the benzotriazole skeleton then introduced into polysiloxane molecules by cohydrolysis with chlorosilanes or alkoxysilanes (Unexamined Published Japanese Patent Application No. 57-21391).

When this method was applied to polysiloxanes without reactive functional groups, however, the benzotriazole type compound tended to be hydrolyzed due to the presence of the alkoxysilyl groups, and it lacked stability. In particular when these hydrolyzable substances were used for medical or cosmetic applications, moreover, the hydrolysis products had an irritating effect on the skin and membranes.

Another method has been proposed whereby the phenolic hydroxyl groups of compounds with a benzotriazole skeleton have been utilized to make alkyl ether derivatives with vinylsilyl groups, and hydrosilylation carried out on these vinyl groups so as to introduce benzotriazole type compounds into polysiloxane molecules (Unexamined Published Japanese Patent Application No. 63-230681).

In the case of compounds with this alkyl phenyl ether skeleton, however, radical cleavage via quinone intermediates tended to occur when ultraviolet radiation was absorbed or showed a tendency to hydrolysis under acidic conditions, and stability was poorer than in the case of alkylation via carbon-carbon bonds.

As described above, despite the fact that the use of silicone oils has been increasing in recent years in the medical and cosmetic fields, compounds which are alkyl modified via carbon-carbon bonding with a benzotriazole compound so as to introduce the benzotriazole skeleton into a polysiloxane molecule, or compounds which do not have hydrolyzable alkoxysilyl groups, which are stable and yet are highly soluble in silicone oils, had still not been obtained.

SUMMARY OF THE INVENTION

The aim of this invention is therefore to provide novel ultraviolet absorbing agents which have excellent solubility in substrates, and especially in silicone oils.

The above object is achieved by organosilicon compounds represented by the general formula:

and a preparing process for the preparation thereof; where a lies in the range $1 \leq a \leq 3$ and b lies in the range $0.001 \leq b \leq 2$, $R^1$ are identical or dissimilar monovalent saturated or unsaturated hydrocarbons with 1–30 carbon atoms,

$R^2$ is a monovalent organic group represented by the formula $-(-CR^3_2CR^3(H)CR^3_2-)-R^4$, $R^3$ are hydrogen atoms or monovalent saturated hydrocarbon groups with 1–5 carbon atoms, $R^4$ are groups represented by the formula:

or:

$R^5$ being identical to said $R^1$ or halogen atoms, alkoxy groups, carboxyl groups, hydroxyl groups or amino groups, d is an integer from 0 to 4, and c is an integer from 0 to 3.

The organosilicon compounds of this invention have an ultraviolet absorbing benzotriazole skeleton, and they are therefore extremely useful as blending agents in the medical and cosmetic fields, and as additives to plastics.

DETAILED DESCRIPTION OF THE INVENTION

The novel organosilicon compounds of this invention which is represented by the general formula $$R^1{}_a R^2{}_b SiO_{\frac{4-a-b}{2}},$$

may be synthesized by a rearrangement reaction according to known methods to obtain an allylation precursor, and then carrying out a hydrosilylation. The benzotriazole type ultraviolet absorption agent which is the starting material may be represented by the general formula:

typical compounds of this type being:

2-(2'-hydroxy-5'-methylphenyl) benzotriazole,

2-(2'-hydroxy-5'-tert-octylphenyl) benzotriazole,

2-(2'-hydroxy-5'-tert-butylphenyl) benzotriazole,

2-(2'-hydroxyphenyl) benzotriazole,

2-(2'-hydroxyphenyl)-5-chlorobenzotriazole, 2-(2',4'-dihydroxyphenyl)-5-chlorobenzotriazole, 2-(2'-hydroxyphenyl)-5-carboxybenzotriazole, and 2-(2'-hydroxy-5'-tert-butylphenyl)-5-aminobenzotriazole.

The phenolic hydroxyl parts of these compounds are allyl etherified under basic conditions, and the allylated benzotriazole derivative:

or is then obtained by a heat-induced rearrangement reaction.

To promote the rearrangement of the allyl ether, it is a necessary condition that either the ortho or para position with respect to the phenolic —OH group of the benzotriazole type compound which is the starting material, is unsubstituted.

The allylated benzotriazole derivative thus obtained is then made to undergo an addition reaction with an organohydrogen silane or an organohydrogen polysiloxane represented by the general formula:

using catalyst such as platinic compound, palladic compound or rhodium compound so as to obtain the novel organosilicon compound of this invention represented by the general formula:

In this formula, $R^1$ are identical or dissimilar saturated or unsaturated hydrocarbon groups with 1-30 carbon atoms. Examples of $R^1$ are saturated aliphatic hydrocarbon groups such as methyl, ethyl, propyl, butyl, pentyl, hexyl, heptyl, octyl, nonyl and decyl; saturated alicyclic hydrocarbon groups such as cyclopentyl and cyclohexyl; unsaturated hydrocarbon groups such as vinyl and allyl; and aromatic hydrocarbon groups such as phenyl and tolyl. It is however particularly preferable that methyl groups account for no less than 50 mol % of $R^1$.

$R^2$ in this formula, is a monovalent organic group represented by the formula $-(-CR^3{}_2CR^3(H)CR^3{}_2-)-R^4$; $R^3$ is a hydrogen or a monovalent saturated hydrocarbon group with 1-5 carbon atoms; and $R^4$ is a group containing the benzotriazole skeleton and represented by the formula:

or $R^5$ is the same as $R^1$, or is chosen from a halogen atom such as fluorine, chlorine or bromine, alkoxy groups with 1-10 carbon atoms, carboxyl, hydroxyl, and amino groups.

Also in this formula, a lies in the range 1.0-3.0 and preferably in the range 1.5-2.5; b lies in the range 0.001-2.0 and preferably in the range 0.01-1.0. If a is less than 1.0, sufficient solubility in silicone substrates is not obtained, while if it is greater than 3.0, the content of the group $R^2$ which is effective for ultraviolet absorption cannot be sufficient. Further, if b is less than 0.001, the content of the group $R^2$ which is effective for ultraviolet absorption cannot be sufficient, while if it is greater than 2.0, sufficient solubility in silicone substrates is not obtained.

Finally, in this formula, d is an integer lying in the range 0-4, and c is an integer lying in the range 0-3.

The organosilicon compounds of this invention not only have a high ultraviolet absorption coefficient, but also have a high solubility in silicone oils. Ultraviolet absorption properties may therefore be imparted easily to silicone oils by adding these compounds to them. Further, these compounds do not contain alkoxy or other reactive groups attached to the silicon atoms, they are stable and they do not cause much irritation to the skin. They will therefore prove particularly useful when applied to cosmetic preparations.

EXAMPLES

We shall now describe this invention in more detail with reference to specific examples, but it should be understood that the invention is by no means limited to them.

EXAMPLE 1

The above reagent I (98.4 g) and toluene (250 g) were introduced into a reaction vessel, and the mixture was stirred for 30 min. while gradually adding a 28 weight % solution of sodium methoxide in methanol (127 g) by means of a dropping funnel. Next, the internal temperature was raised to 70°-85° C. and after removing 100 g of solvent, the internal temperature was lowered to 40° C. by air-cooling, and allyl bromide (106.4 g) was added gradually by means of a dropping funnel. After the addition was complete, the salt produced by refluxing for 2 hours was filtered and washed with water. After again removing solvent under reduced pressure, the residue was distilled under reduced pressure.

During this distillation, a rearrangement reaction was carried out under full reflux without collecting any fractions until the temperature rose to over 200° C. In this way, 106.4 g of a rearrangement fraction was obtained directly in the temperature range 211°-222° C. at a reduced pressure of 7 mmHg without isolating the allyl ether intermediate. This fraction was recrystallized from 1,000 g of a mixed solvent of toluene and methanol in the proportion (by weight) of 1:9, so as to obtain the allyl derivative represented by the formula:

This consisted of white needle-like crystals of melting point 100°-102° C., yield 87.9 g.

Next, the above allyl derivative (30 g) was introduced into a reaction vessel together with 2-propanol (150 g), a 10 weight % solution of potassium acetate in ethanol (0.3 g) and a 2 weight % chloroplatinic acid solution in 2-propanol (0.05 g), and after raising the internal temperature to 80° C., 49.8 g of the following methyl hydrogen polysiloxane reagent;

(II)

$$\begin{array}{c} CH_3 \\ | \\ HSi-O \\ | \\ CH_3 \end{array} \left[ \begin{array}{c} CH_3 \\ | \\ Si-O \\ | \\ CH_3 \end{array} \right]_3 \begin{array}{c} CH_3 \\ | \\ Si-CH_3 \\ | \\ CH_3 \end{array}$$

was gradually added by means of a dropping funnel. After the addition was complete, the resulting mixture was stirred for 8 hours while maintaining the internal temperature at 80°–90° C.

The reaction solution was air-cooled to room temperature, 0.5 g of active carbon was added and stirring was continued for 2 hours. After filtering off the active carbon, the solution was heated to 150° C. under reduced pressure (5 mmHg) for 2 hours to remove solvent and unreacted methylhydrogenpolysiloxane, and the desired organosilicon compound:

was obtained. This consisted of a yellow transparent liquid of viscosity 54.8 cs at 25° C., yield 70.0 g.

Figure 1:
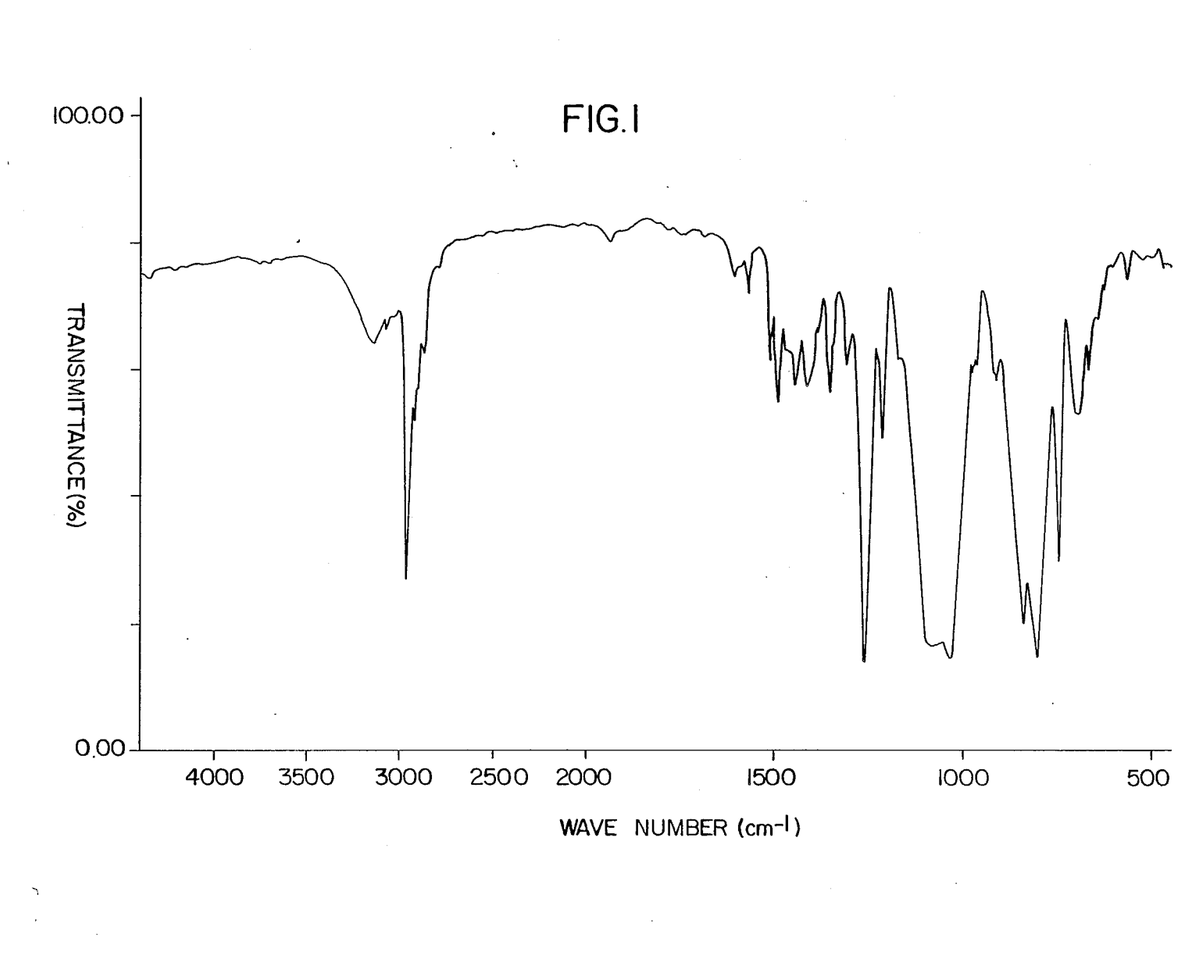
FIG. 1 shows the infrared absorption spectra of the organosilicon compound of the present invention which was obtained in Example 1.
Figure 2:
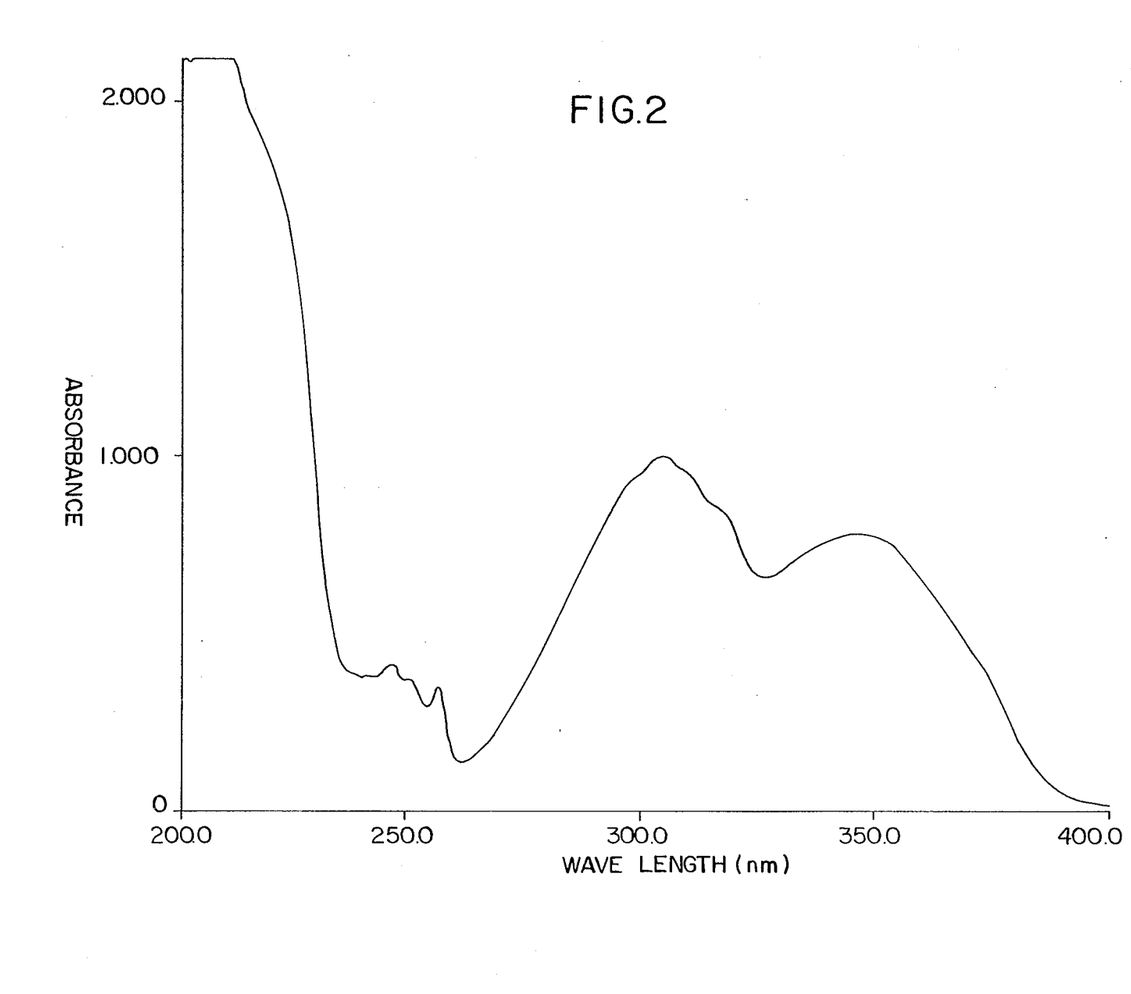
FIG. 2 shows the ultraviolet absorption spectra of the organosilicon compound of the present invention which was obtained in Example 1.

FIG. 1 and FIG. 2 respectively show the infrared and ultraviolet absorption spectra of the product, while Table 1 shows its solubility in various silicone oils.

Infrared absorption spectra were measured by a Perkin-Elmer Inc. 1640 Fourier Transformation Infrared Spectroscope using KBr plates, while ultraviolet absorption spectra were measured by a Hitachi U-3200 Auto-Recording Spectrophotometer using cyclohexane as solvent, a solute concentration of 4.3 mg/100 ml, and an optical path length in the sample of 1 cm.

TABLE 1

Solubilities in silicone oils of the organosilicon compounds obtained in the examples using a 10 weight % addition of the compounds at room temperature

| silicone oils (viscosity at 25° C.) | organosilicon compounds of this invention | | | |
|---|---|---|---|---|
| | EXAMPLE 1 | EXAMPLE 2 | EXAMPLE 3 | EXAMPLE 4 |
| octamethylcyclotetrasiloxane | homogeneous soln. (transparent) | homogeneous soln. (transparent) | homogeneous soln. (transparent) | homogeneous soln. (transparent) |
| dimethylpolysiloxane (viscosity: 10 cs) | homogeneous soln. (transparent) | homogeneous soln. (transparent) | homogeneous soln. (transparent) | homogeneous soln. (transparent) |
| dimethylpolysiloxane (viscosity: 300 cs) | homogeneous soln. (transparent) | homogeneous soln. (transparent) | white suspension | homogeneous soln. (transparent) |
| dimethylpolysiloxane (viscosity: 1,000 cs) | homogeneous soln. (transparent) | homogeneous soln. (transparent) | white suspension | homogeneous soln. (transparent) |
| dimethylpolysiloxane (viscosity: 10,000 cs) | homogeneous soln. (transparent) | homogeneous soln. (translucent) | white suspension | homogeneous soln. (transparent) |
| methylphenylpolysiloxane (phenyl group content: 5 mole %, viscosity: 200 cs) | homogeneous soln. (transparent) | homogeneous soln. (transparent) | homogeneous soln. (transparent) | homogeneous soln. (transparent) |
| methylphenylpolysiloxane (phenyl group content: 25 mole %, viscosity: 400 cs) | homogeneous soln. (translucent) | white suspension | homogeneous soln. (translucent) | homogeneous soln. (translucent) |
| methylalkylpolysiloxane*[1] (viscosity: 100 cs) | homogeneous soln. (transparent) | white suspension | homogeneous soln. (translucent) | homogeneous soln. (transparent) |
| methyltrifluoropropyl-polysiloxane (trifluoropropyl group content: 15 mole %, viscosity: 36 cs) | homogeneous soln. (transparent) | homogeneous soln. (transparent) | white suspension | homogeneous soln (transparent) |

$$*^1(CH_3)_3SiO-\left(SiO\right)_{\overline{78}}Si(CH_3)_3$$ 
with $C_8H_{17}$ and $CH_3$ substituents

EXAMPLE 2

(III)

An allyl ether derivative was synthesized using the above reagent III (100 g), toluene (250 g), a 28 weight % solution of sodium methoxide in methanol (107 g) and allyl bromide (89.5 g) according to the same procedure as in Example 1, and 104 g of a distillation fraction was obtained by distillation under reduced pressure (5 mmHg) in the temperature range 204°–210° C. The fraction was recrystallized from 1,000 g of a mixed solvent of toluene and methanol in the proportion (by weight) of 15:85, so as to obtain the allyl derivative represented by the formula:

This consisted of light yellow needle-like crystals of melting point 101°–104° C., yield 74.7 g.

Next, this allyl derivative (10 g) was introduced into a reaction vessel together with toluene (70 g) and a 2 weight % chloroplatinic acid solution in 2-propanol (0.02 g), and after raising the internal temperature to 80° C., 52.8 g of the following methylhydrogenpolysiloxane reagent;
average formula (IV)

was gradually added by means of a dropping funnel.

After the addition was complete, the resulting mixture was stirred for 8 hours while maintaining the internal temperature at 80°–90° C.

The reaction solution was air-cooled to room temperature, 0.5 g of active carbon was added and stirring was continued for 2 hours. After filtering off the active carbon, the solution was heated to 150° C. under reduced pressure (5 mmHg) for 2 hours to remove solvent, and the desired organosilicon compound was obtained. This consisted of a yellow transparent liquid of viscosity 425 cs at 25° C., yield 58.0 g.

Figure 3:
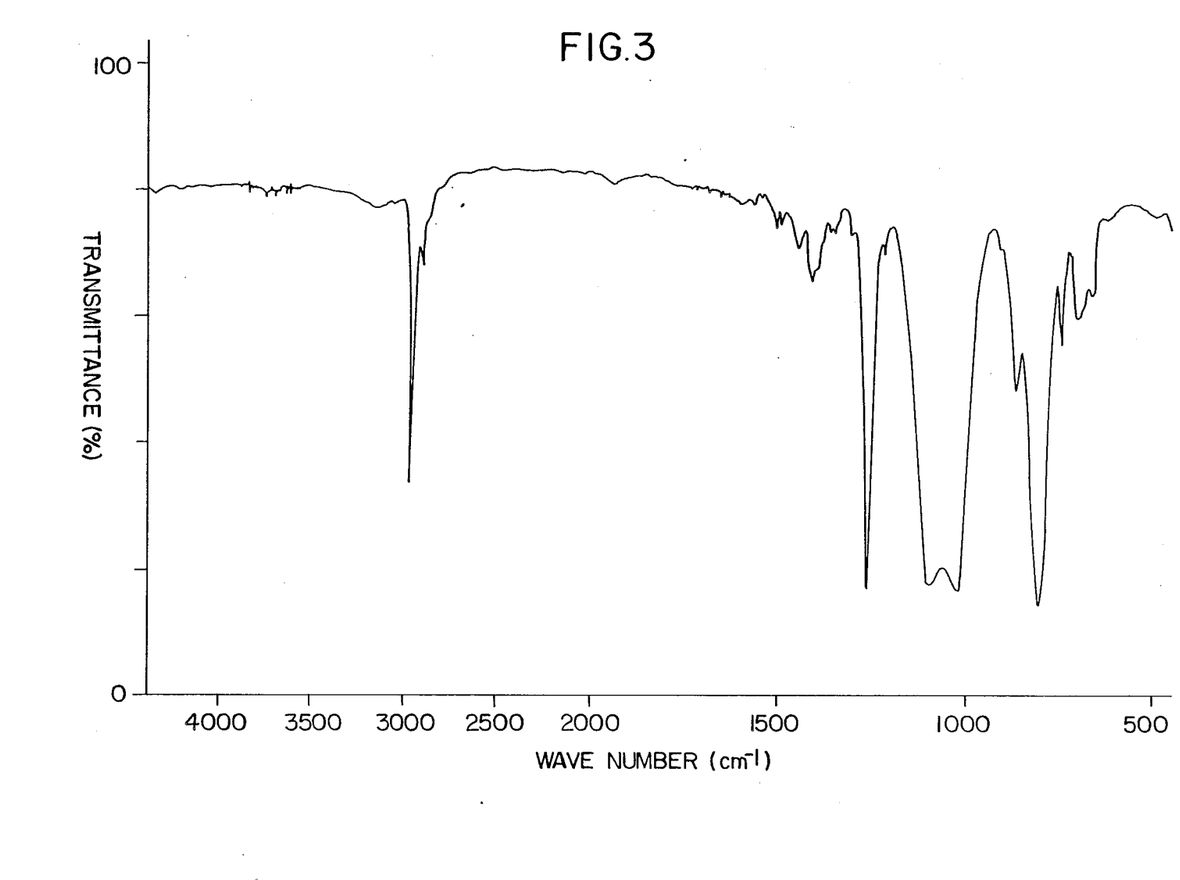
FIG. 3 shows the infrared absorption spectra of the organosilicon compound of the present invention which was obtained in Example 2.
Figure 4:
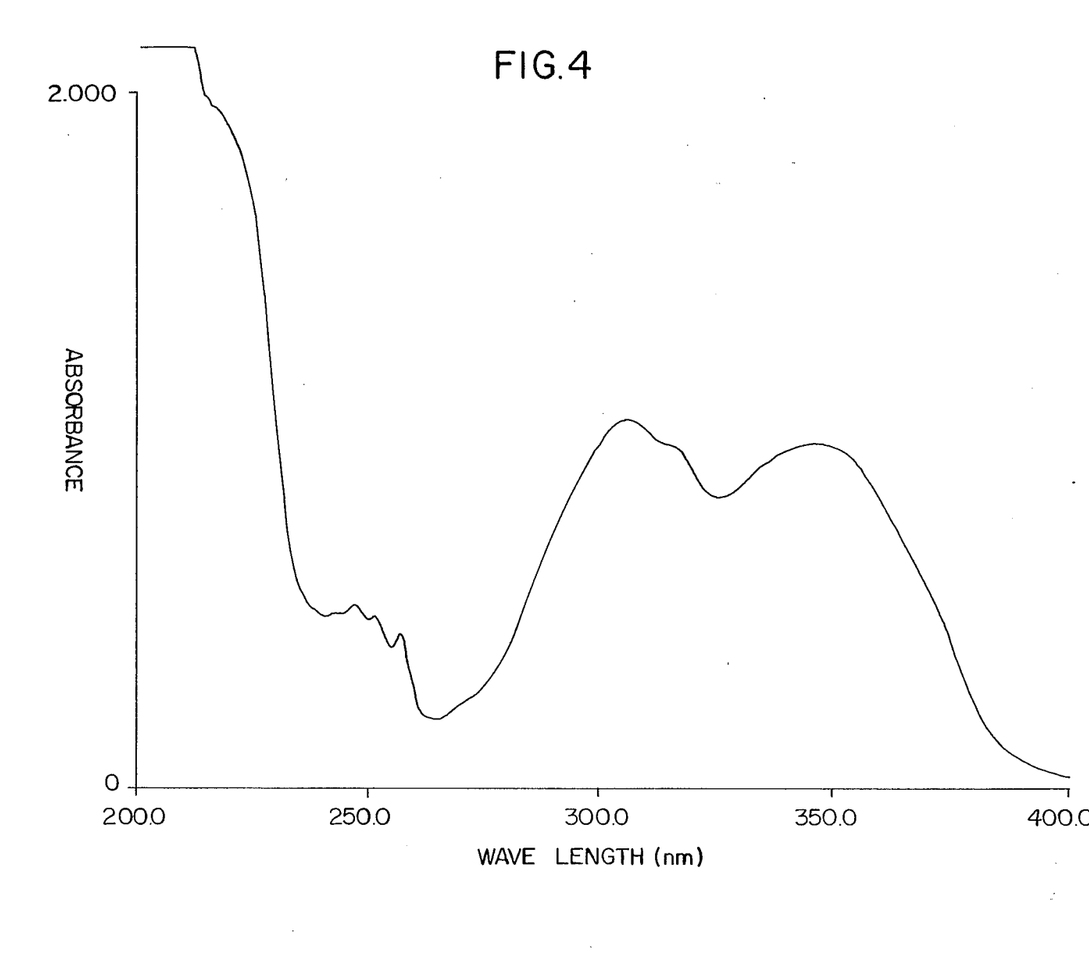
FIG. 4 shows the ultraviolet absorption spectra of the organosilicon compound of the present invention which was obtained in Example 2.

FIG. 3 and FIG. 4 respectively show the infrared and ultraviolet absorption spectra of the product measured as in Example 1, while Table 1 shows its solubility in various silicone oils. The solute concentration of the sample used for measuring ultraviolet absorption spectra was 6.6 mg/100 ml.

EXAMPLE 3

(V)

An allyl ether derivative was synthesized using the above reagent V (80 g), toluene (300 g), a 28 weight % solution of sodium methoxide in methanol (71.6 g) and allyl bromide (45.3 g) according to the same procedure as in Example 1, and 82.0 g of a distillation fraction was obtained by distillation under reduced pressure in the temperature range 243°–246° C. (pressure 5 mmHg). The fraction was recrystallized from 1,750 g of a mixed solvent of toluene and methanol in the proportion (by weight) of 2:33, so as to obtain the allyl derivative respresented by the formula:

This consisted of white crystals of melting point 76°–79° C., yield 64.0 g.

Next, this allyl derivative (15 g) was introduced into a reaction vessel together with toluene (50 g) and a 2 weight % chloroplatinic acid solution in 2-propanol (0.02 g), and using 21.2 g of the following methylhydrogenpolysiloxane reagent; average formula

(VI)

a desired organosilicon compound was obtained as in Example 2. This consisted of a yellow transparent liquid of viscosity 1,110 cs at 25° C., yield 33.4 g.

Figure 5:
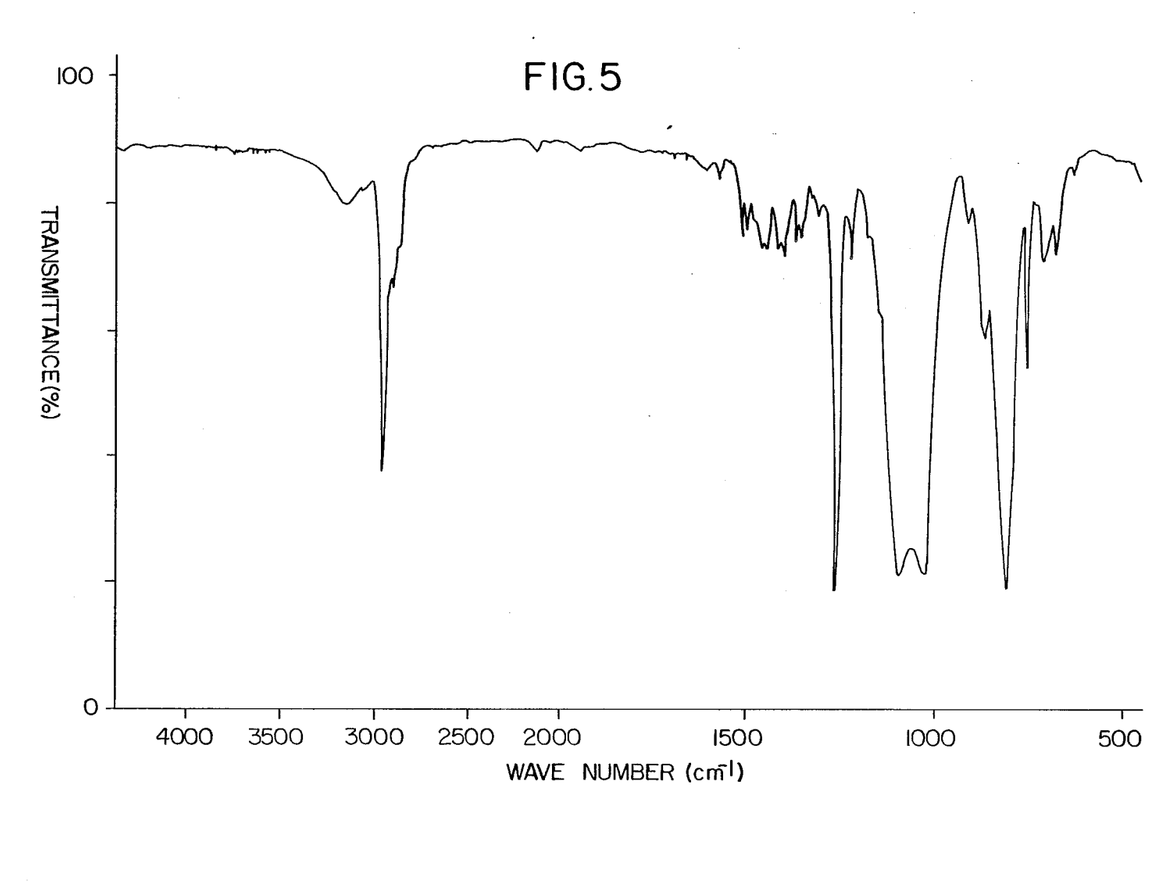
FIG. 5 shows the infrared absorption spectra of the organosilicon compound of the present invention which was obtained in Example 3.
Figure 6:
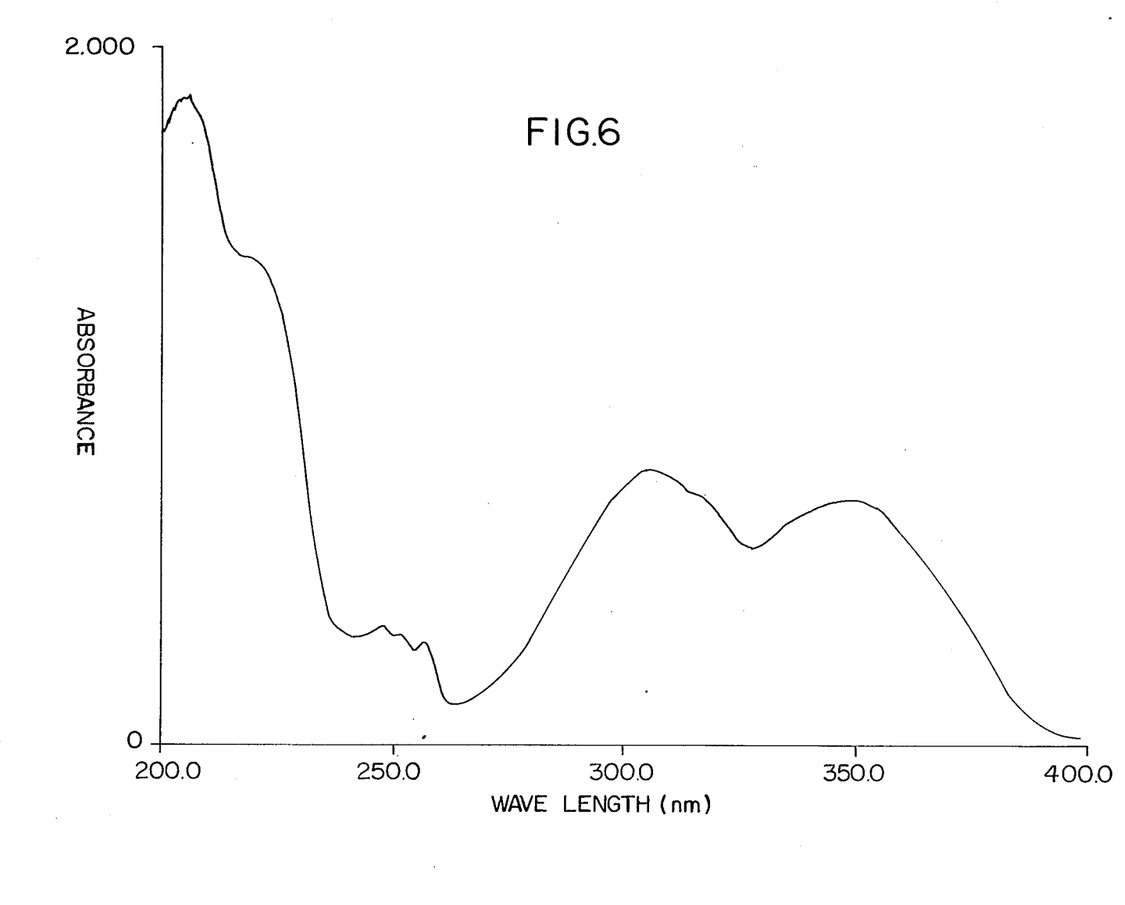
FIG. 6 shows the ultraviolet absorption spectra of the organosilicon compound of the present invention which was obtained in Example 3.

FIG. 5 and FIG. 6 respectively show the infrared and ultraviolet absorption spectra of the product measured as in Example 1, while Table 1 shows its solubility in various silicone oils.

The solute concentration of the sample used for measuring ultraviolet absorption spectra was 4.2 mg/100 ml.

EXAMPLE 4

(VII)

(VIII)

Using the allyl derivative VII (40 g) synthesized in Example 3, toluene (100 g), a 2 weight % solution of chloroplatinic acid in 2-propanol (0.06 g) and the above reagent VIII (49 g), a desired organosilicon compound was obtained as in Example 2. This consisted of a yellow transparent liquid of viscosity 318 cs at 25° C., yield 79.7 g.

Figure 7:
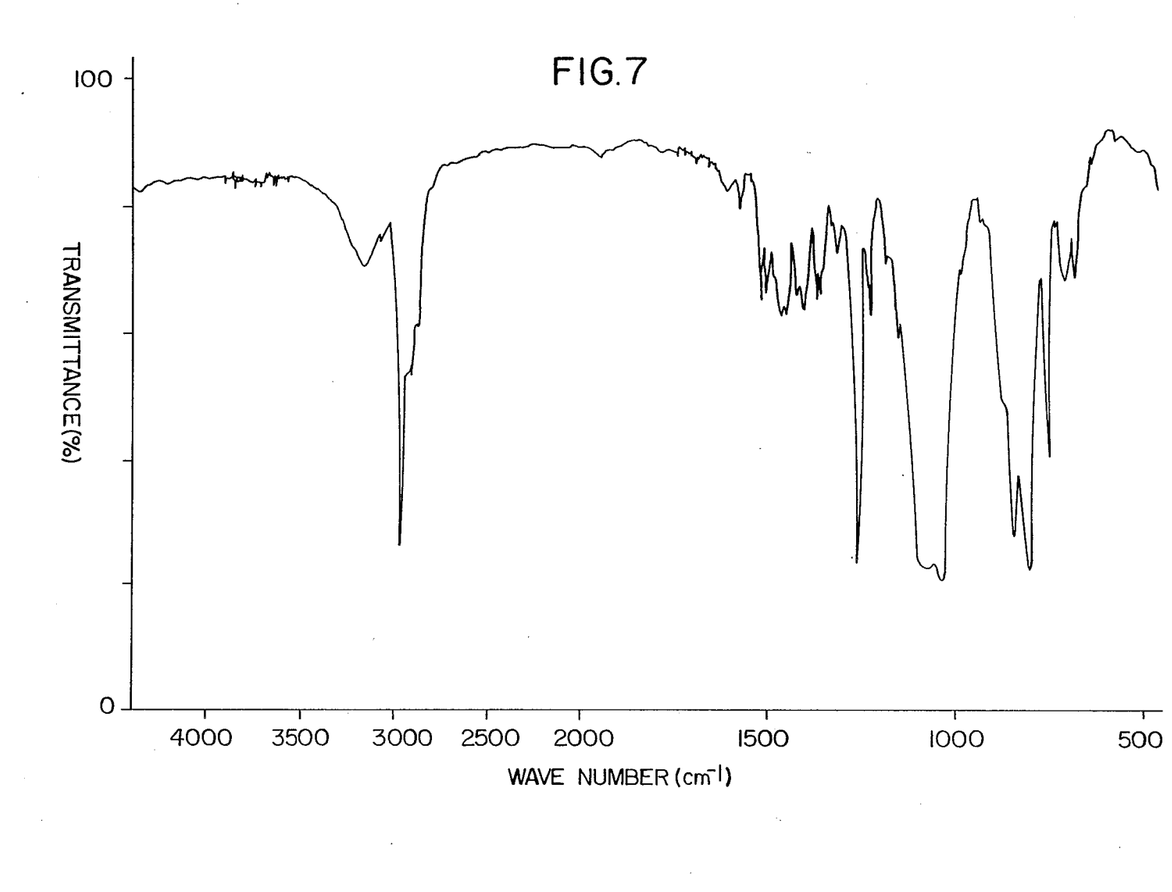
FIG. 7 shows the infrared absorption spectra of the organosilicon compound of the present invention which was obtained in Example 4.
Figure 8:
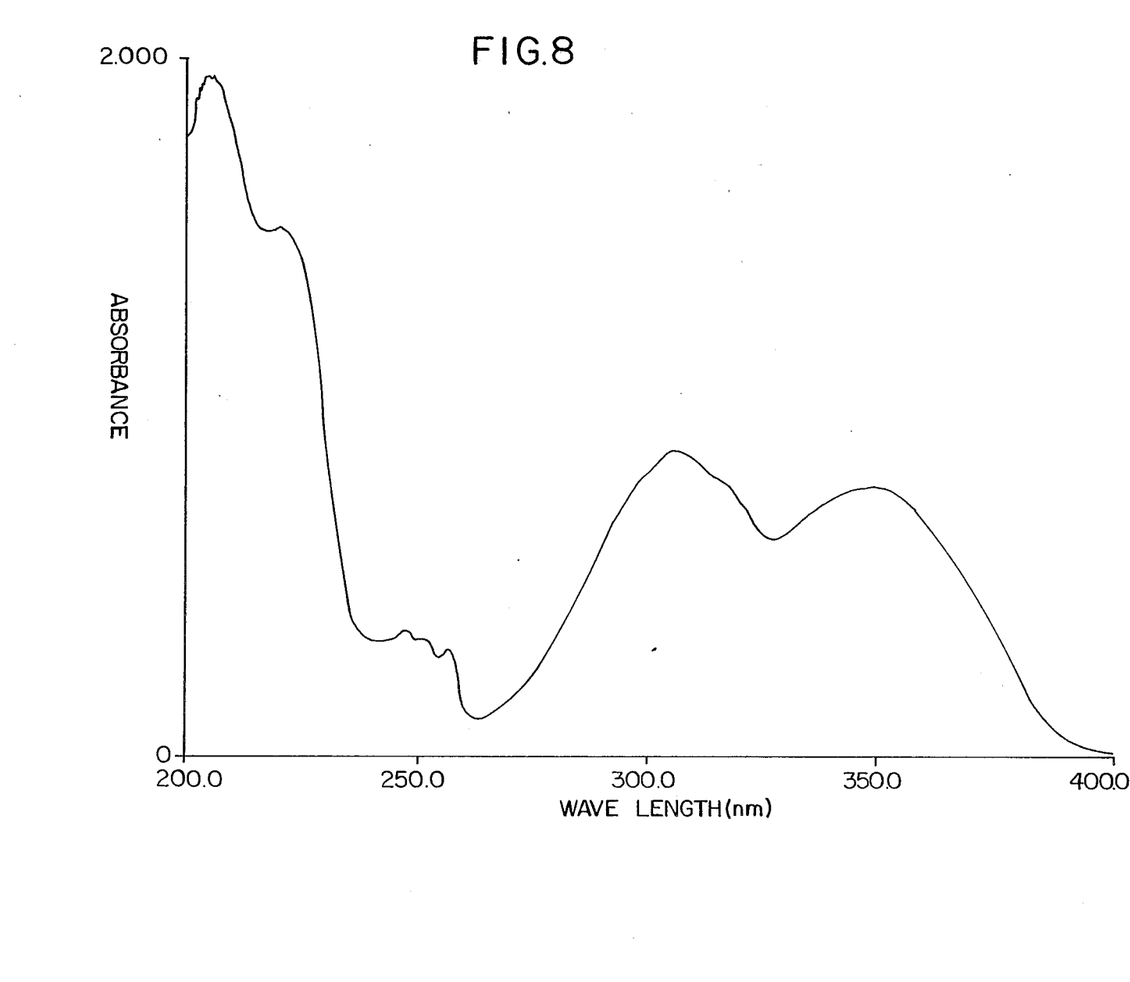
FIG. 8 shows the ultraviolet absorption spectra of the organosilicon compound of the present invention which was obtained in Example 4.

FIG. 7 and FIG. 8 respectively show the infrared and ultraviolet absorption spectra of the product measured as in Example 1, while Table 1 shows its solubility in various silicone oils.

The solute concentration of the sample used for measuring ultraviolet spectra was 3.9 mg/100 ml.

EXAMPLE 5

(IX)

(X)

Using the allyl derivative IX (15 g) synthesized in Example 1, 2-propanol (150 g), a 10 weight % solution of potassium acetate in ethanol (0.3 g), a 2 weight % solution of chloroplatinic acid in 2-propanol (0.03 g) and the above methylphenylhydrogendisiloxane reagent X (15.4 g), a desired organosilicon compound was obtained as in Example 1. This consisted of a yellow translucent liquid of viscosity 895 cs at 25° C., yield 27.0 g.

Figure 9:
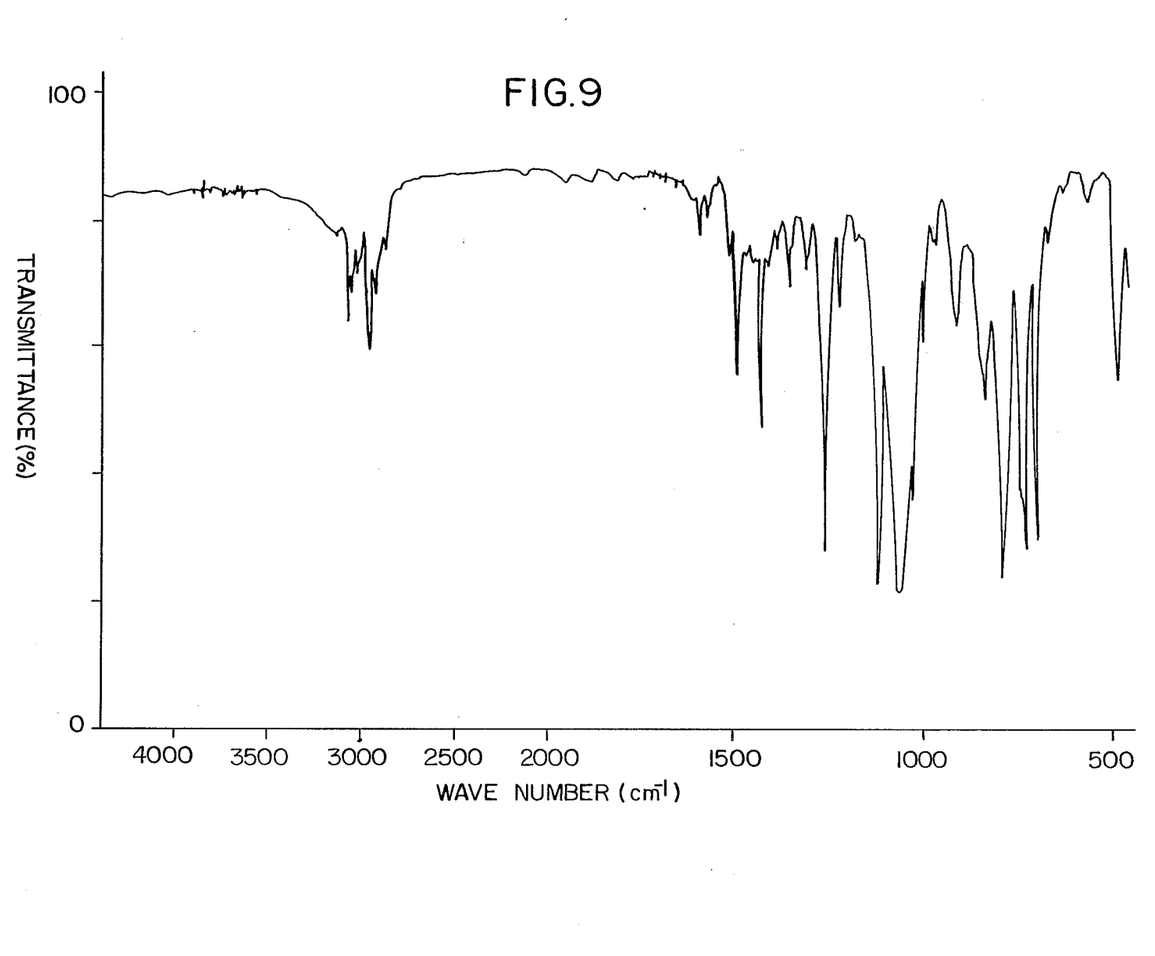
FIG. 9 shows the infrared absorption spectra of the organosilicon compound of the present invention which was obtained in Example 5.
Figure 10:
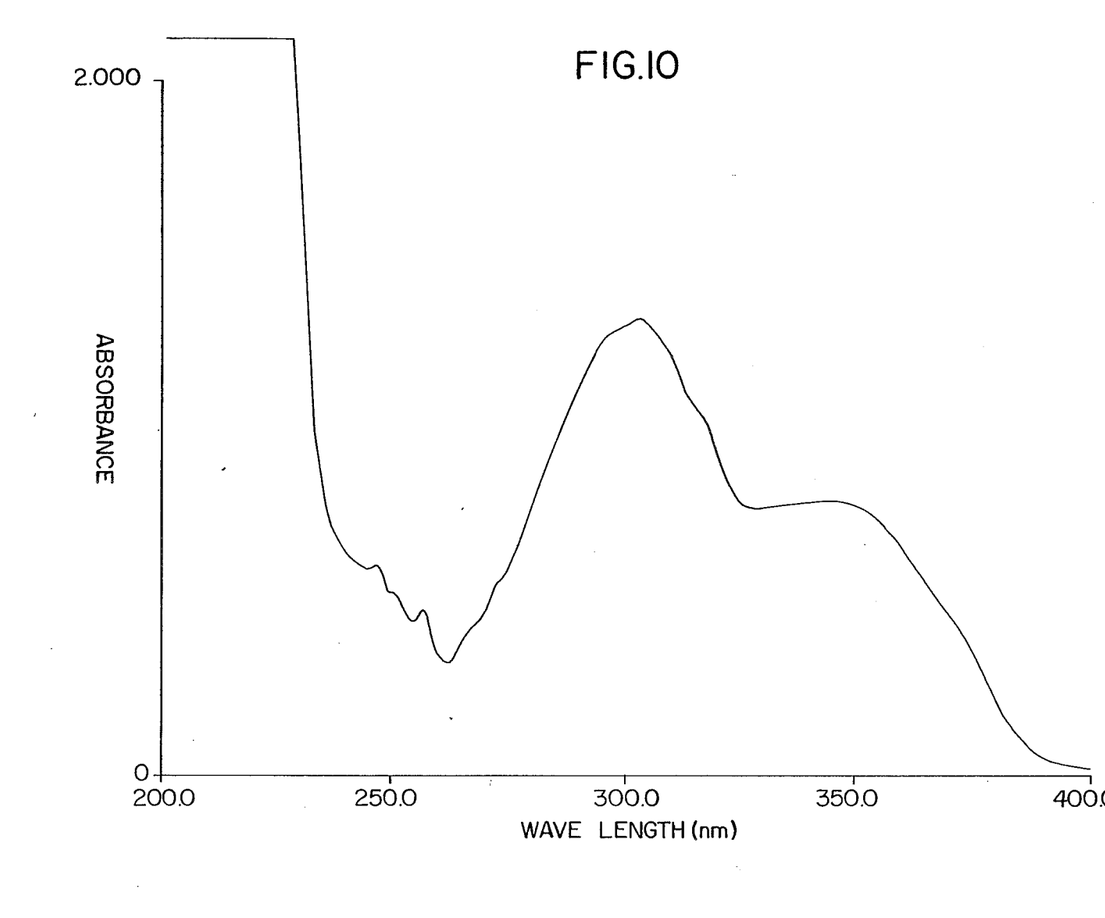
FIG. 10 shows the ultraviolet absorption spectra of the organosilicon compound of the present invention which was obtained in Example 5.

FIG. 9 and FIG. 10 respectively show the infrared and ultraviolet absorption spectra of the product measured as in Example 1.

The solute concentration of the sample used for measuring ultraviolet absorption spectra was 5.9 mg/100 ml.

Further, when the product was added, in the proportion of 10 weight %, to a methylphenylpolysiloxane containing 25 mole % of phenyl groups and having a viscosity of 400 cs, and a methylphenylpolysiloxane containing 28 mole % of phenyl groups and having a viscosity of 15 cs respectively, it dissolved homogeneously at room temperature to give transparent solutions in both cases.

This confirmed that whereas only minute quantities of benzotriazole type compounds dissolve in silicone oils, the organosilicon compounds obtained in this invention have a very high solubility while also strongly absorbing ultraviolet radiation.

What is claimed is:

1. Organosilicon compounds represented by the general formula:

where a lies in the range $1 \leq a \leq 3$ and b lies in the range $0.001 \leq b \leq 2$, $R^1$ are identical or dissimilar monovalent saturated or unsaturated hydrocarbons with 1–30 carbon atoms,

$R^2$ is a monovalent organic group represented by $-(CR^3{}_2CR^3(H)CR^3{}_2)-R^4$, $R^3$ are hydrogen atoms or monovalent saturated hydrocarbon groups with 1–5 carbon atoms, $R^4$ are monovalent organic groups represented by the formula:

or:

$R^5$ being identical to said $R^1$ or halogen atoms, alkoxy groups, carboxyl groups, hydroxyl groups or amino groups, d is an integer from 0 to 4 and c is an integer from 0 to 3.

2. The organosilicon compounds of claim 1, wherein $R^1$ is selected from the group consisting of saturated aliphatic hydrocarbon groups, saturated alicyclic hydrocarbon groups, unsaturated hydrocarbon groups and aromatic hydrocarbon groups.

3. The organosilicon compounds of claim 2, wherein $R^1$ is methyl, ethyl, propyl, butyl group, pentyl, hexyl, heptyl, octyl group, nonyl or decyl.

4. The organosilicon compounds of claim 2, wherein $R^1$ is a cyclopentyl or cyclohexyl group.

5. The organosilicon compounds of claim 2, wherein $R^1$ is a vinyl or allyl group.

6. The organosilicon compounds of claim 2, wherein $R^1$ is a phenyl or tolyl group.

7. The organosilicon compounds of claim 1, wherein methyl groups account for no less than 50 mol % of $R^1$.

8. The organosilicon compounds of claim 1, wherein a lies in the range $1.5 \leq a \leq 2.5$.

9. The organosilicon compounds of claim 1, wherein b lies in the range $0.01 \leq b \leq 1.0$.

* * * * *